(12) United States Patent
Wagner et al.

(10) Patent No.: US 8,424,718 B2
(45) Date of Patent: Apr. 23, 2013

(54) METHOD OF MIXING AND EXTRUDING VISCOUS MATERIALS AND GEARBOX FOR DISPENSING THE SAME

(75) Inventors: Ingo W. Wagner, Wörthsee (DE); Manfred Harre, Landsberg am Lech (DE); Hansjoerg Spitschan, Herrsching (DE)

(73) Assignee: 3M Deutschland GmbH, Neuss (DE)

( * ) Notice: Subject to any disclaimer, the term of this patent is extended or adjusted under 35 U.S.C. 154(b) by 3 days.

(21) Appl. No.: 12/977,714

(22) Filed: Dec. 23, 2010

(65) Prior Publication Data

US 2011/0095048 A1    Apr. 28, 2011

Related U.S. Application Data

(63) Continuation of application No. 11/718,731, filed as application No. PCT/EP2005/011940 on Nov. 8, 2005, now abandoned.

(30) Foreign Application Priority Data

Nov. 9, 2004   (EP) .................................... 04026576

(51) Int. Cl.
*B67D 7/64*   (2010.01)
(52) U.S. Cl.
USPC ............ 222/1; 222/333; 222/145.5; 222/135; 222/326
(58) Field of Classification Search .................. 222/333, 222/135, 137, 63, 145.6, 1, 325, 326, 386, 222/390; 74/661, 664; 173/216, 217, 93, 173/93.5, 176
See application file for complete search history.

(56) References Cited

U.S. PATENT DOCUMENTS

| 3,019,669 | A | * | 2/1962 | Cozzo et al. ..................... 74/661 |
| 3,213,711 | A |  | 10/1965 | Van Den Kieboom |
| 3,561,544 | A | * | 2/1971 | Farmer ......................... 173/145 |
| 3,586,115 | A | * | 6/1971 | Amtsberg et al. ............... 173/33 |
| 4,147,219 | A | * | 4/1979 | Wallace ........................ 173/178 |
| 4,484,871 | A |  | 11/1984 | Adman et al. |
| 4,522,269 | A | * | 6/1985 | Adman et al. ................ 173/177 |
| 4,934,827 | A |  | 6/1990 | Taschke et al. |
| 5,062,547 | A | * | 11/1991 | Zahner et al. .............. 222/144.5 |
| 5,286,105 | A |  | 2/1994 | Herold et al. |
| 5,464,128 | A |  | 11/1995 | Keller |
| 5,556,009 | A | * | 9/1996 | Motzko ......................... 222/326 |
| 5,954,144 | A |  | 9/1999 | Thames |
| 6,168,052 | B1 |  | 1/2001 | Keller |
| 6,311,871 | B1 |  | 11/2001 | Binder |
| 6,321,940 | B1 | * | 11/2001 | Imatomi et al. ................. 222/63 |

(Continued)

FOREIGN PATENT DOCUMENTS

WO   WO 01/53640   7/2001
WO   WO 01/64000   8/2001

*Primary Examiner* — Kevin P Shaver
*Assistant Examiner* — Donnell Long
(74) *Attorney, Agent, or Firm* — Carlos M. Téllez; 3M Innovative Properties Company

(57) ABSTRACT

The present invention relates to a method of mixing and dispensing viscous materials, comprising the steps of: inserting a cartridge containing one or more viscous materials in a chamber; activating a first motor (1) to move a plunger from a first position to a second position within the cartridge and activating a second motor (2) to move the plunger from the second position further within the cartridge to dispense the material.

12 Claims, 6 Drawing Sheets

U.S. PATENT DOCUMENTS

| | | |
|---|---|---|
| 6,371,336 B1 | 4/2002 | Keller |
| 6,457,609 B1 | 10/2002 | Keller |
| 6,837,612 B2 | 1/2005 | Bublewitz et al. |
| 6,854,621 B2 | 2/2005 | Keller |
| 2003/0022128 A1 | 1/2003 | Heymann et al. |
| 2009/0001096 A1 | 1/2009 | Wagner |

* cited by examiner

METHOD OF MIXING AND EXTRUDING VISCOUS MATERIALS AND GEARBOX FOR DISPENSING THE SAME

CROSS-REFERENCE TO RELATED APPLICATIONS

The present application is a continuation of U.S. patent application Ser. No. 11/718,731, filed Nov. 7, 2007 now abandoned, which is a U.S. 371 National Stage Application of PCT/EP2005/011940, filed Nov. 8, 2005, which claims priority from European Patent Application No. 04 02 6576.1, filed Nov. 9, 2004.

BACKGROUND OF THE INVENTION

1. Technical Field

The invention relates to a method of mixing and extruding viscous materials, particularly relatively highly viscous or pasty materials, and to a gearbox, in particular to a superimposing gear drive, for transmitting high torque and/or high revolutions per minute to an output drive shaft without changing gears. The gearbox may particularly be used together with dispensing cartridges and mixer elements for mixing and dispensing multi-component dental impression materials.

2. Description of the Related Art

Dispensing devices with cartridges are often used in the field of dentistry for mixing and dispensing dental compositions of two or more components, such as impression materials, restoratives, adhesives, cements, etching gels, sealants and the like.

In one type of dispensing device that comprises an applicator and a cartridge, the applicator has a plunger that is advanced either manually by the user or automatically by a machine during a dispensing operation. Often, the plunger is received in an open end of the cartridge and bears against a piston within the cartridge. As the plunger is advanced to move the piston, the piston expels or dispenses a quantity of material through a front outlet opening of the cartridge.

The dispensing cartridge of such a device often comprises two compartments that are formed by two cylindrical bodies arranged in parallel to each other. Each compartment contains a specific component, usually either a base paste or a catalyst paste. These two components are pressed from their respective compartments out into a mixing area, or tip, where the components mix to form the required dental material. The pressure further urges the mixture out of the mixing tip so that the dental professional can use it as desired.

One type of such dispensing devices is an assembly (e.g., the Garant™ dispenser available from 3M ESPE AG) that includes a reusable, hand-operated applicator and a disposable cartridge. Another type of such dispensing device is an automatic dispensing system (e.g., Pentamix™ 2 available from 3M ESPE AG) that includes a motor-driven mixing unit and reusable and interchangeable cartridges. The mixing unit comprises a chamber for holding the cartridge, and two parallel, motor-driven plungers designed to plunge into two respective compartments of the cartridge and to exert high pressure on the viscous components contained therein. The motor drive for the plungers provides high torque to extrude the viscous or highly viscous components under high pressure into a mixing tip. Furthermore, the motor also provides a reasonably higher speed to rapidly move the plungers forward and backward within the cartridge when the viscous components are not being extruded. DC motors are generally used in such devices. For example, the motor drives the plungers into a first or "back" position for filling new components into the cartridge and/or inserting new cartridges of components into the machine. After refilling, the plungers are driven into a second or "initial" position, wherein the plungers are in direct or indirect contact with the component(s). When the plungers each contact a component, the resistance, and therefore the load, to the drive increases and a high load is applied to the driving gearbox and motor during the dispensing operation.

It is difficult to achieve both high torque at low speed, and also low torque at high speed, without changing gears. It is also difficult to achieve highly different speeds, e.g., differing by a magnitude of 100, using a linear drive of any kind without changing gears or using clutch-like devices. The changing of gears typically requires a complicated drive. Furthermore, it is very difficult or sometimes even impossible to change gears under load. Devices that can perform these functions can as a result be complicated and expensive.

Furthermore, highly viscous, multi-component mixtures, like dental impression materials, are produced using mixing devices in which the individual components of the mixture are simultaneously supplied from separate cartridge cylinders to a mixer. From the mixing area, the mixture is then dispensed from a front end. The mixer may be a static mixer or, preferably, a dynamic mixer having a rotary mixer element. Known dynamic mixers have at their rear end (inlet side) a central hexagonal opening for coupling to a drive shaft, which shaft rotates the mixer element of the mixer, and the drive shaft is preferably connected to a motor. Accordingly, it is desirable to use a drive unit which can drive also the dynamic mixer in addition to moving the plungers.

It would be desirable to overcome these and/or other disadvantages of known gearboxes and methods of mixing and extruding viscous materials.

SUMMARY OF THE INVENTION

The gearbox according to the invention is adapted to be driven by at least two motors (hereinafter the first motor and the second motor, respectively, although additional motors are not excluded). The gearbox comprises a first output drive shaft, wherein the first output drive shaft provides at least two different driving speeds; hereinafter referred as the lower and higher speeds. The higher speed is preferably in the range of from 30 to 200 times faster than the lower speed, and more preferably in the range of from 80 to 120 times faster than the lower speed. Even more preferably the higher speed is at least 100 times faster than the lower speed. Driving the plunger with the lower speed may result in a standard dispensing speed of 22.5 mm/min. This results in a plunger speed of 2.250 m/min when the motor is driven at a higher speed with a speed transformation ratio of 100, as mentioned above. It may be provided that the dispensing speed is about two times the standard dispensing speed, i.e., 45 mm/min or any other value in-between such as 33 mm/min. During the lower speed a normal load is usually applied when extruding the materials and during the higher speed a load is applied which is generally just needed to move the plunger without pushing against the materials. The first output drive shaft can be driven by the first motor and/or by the second motor to provide the at least two different speeds. Furthermore, if the first output drive shaft is driven by the first and second motor at the same time, the output drive shaft speed will be the sum or the difference of the two driving speeds of the motors, depending on the ratios of the gears of the gearbox and the rotation directions of the motors. For example, if the gearbox has a first transmission ratio between the speeds of the first output drive shaft and the first motor with the second motor standing still, and a second transmission ratio between the speeds of the first output drive shaft and the second motor with the first motor standing still, then the first output drive shaft speed is the sum (or the difference, depending on the rotation directions of the motors) of a first transmitted speed of the first motor and a second transmitted speed of the second motor. In this case the first and second transmitted speeds are the products of the first or second transmission ratios and the first or second motor speeds, respectively. Each motor may be a variable-speed motor or a constant-speed motor. Thus, it may be provided that the two motors are permanently connected with the output drive shaft via the gearbox. In case that only one motor is driven, i.e. one input shaft is rotating the other motor prevents the second input shaft from rotating such that a force can be transmitted from the first input shaft to the output shaft.

The gearbox of the invention preferably comprises a superimposing gear drive. Examples of useful superimposing gear drives include bevel gear drives, differential gear drives and planetary gear drives.

A superimposing gear drive comprises, in principle, at least three different kinds or groups of gears or gear wheels, which are hereinafter referred to as the first gear/gear wheel, second gear/gear wheel and third gear/gear wheel. The third gear is arranged in engagement with the first and second gear wherein a carrier preferably carries the third gear. In case of a planetary gear drive the first, second and third gear would correspond to the inner gear, outer gear and planetary gear, respectively. In the planetary gear drive the carrier is hereinafter also referred as planet carrier. Typically, a planetary gear drive comprises at least one planetary gear, and preferably a plurality of planetary gears that may be connected to each other by a planet carrier. The planetary (third) gears are arranged in engagement with the inner gear and the outer gear. The inner (first) gear, the outer (second) gear and the planet carrier may be connected to a drive connection which could be either a input drive connection or an output drive connection.

The superimposing gear drive of the present invention uses two drive connections as input drives, each connected to a motor, and one drive connection is connected to a first output drive shaft. The torque and the speed of the two input drive connections are superimposed in the superimposing gear drive. The three kinds or groups of gears of the superimposing gear drive, as discussed above, are movable. A variable output speed at the first output drive shaft is obtained by vectorially adding or subtracting the speeds provided by the first and second motors.

The embodiment of a planetary gear drive comprises at least an inner planetary gear often called sun gear, an outer planetary gear which is called the annulus gear or ring gear and at least one planet gear, wherein a planet carrier supports at least one planet gear. Therefore, the planetary gear drive provides at least three drive connections, one in connection to the inner gear, one in connection to the outer gear and one in connection to the planet carrier. In the embodiment of a bevel gear, most of the gears/gear wheels are beveled and the inner gear may have the same size or a similar shape as the outer gear.

According to a first aspect of the invention, a gearbox is adapted to be driven by at least a first motor and a second motor and comprises at least a first output drive shaft. The gearbox is adapted to drive the first output drive shaft with a higher torque when driven with the second motor than when driven with the first motor. Moreover the gearbox is adapted to drive the first output drive shaft with a higher speed or more revolutions per minute when driven with the first motor than when driven with the second motor.

It may be provided that the speed of the first output drive shaft is the sum or difference of the first motor and the second motor.

Preferably the drive connections of the first gear and the second gear are selected as the two input drive connections, which are connected to a second motor and to a first motor, respectively. The drive connection of the carrier is selected as the first output drive shaft which provides different speeds and different torques according to the two motors which drive the gearbox at the two input drive connections. The second motor is adapted to drive the first gear, and the first motor is adapted to drive the second gear. Due to the different gear transmission ratios from the first motor and the second motor to the carrier and therefore to the first output drive shaft, the first output drive shaft is driven to provide high torque, by driving the first gear of the gear drive with the second motor. On the other hand, when high revolutions per minute are needed and less torque is sufficient, the second gear is driven by the first motor, which provides higher revolutions per minute at the first output drive shaft.

According to a second aspect of the invention, the drive connections of the carrier and the second gear are selected as the two input drive connections. The drive connection of the carrier is connected to the second motor and the drive connection of the second gear is connected to the first motor. The first output drive shaft is connected to the first gear and provides different speeds and different torques according to the two motors which drive the gearbox at the two input drive connections. The second motor is adapted to drive the carrier and the first motor is adapted to drive the second gear. Due to the different gear transmission ratios, the first output drive shaft is driven to provide high torque, by driving the carrier of the gearbox with the second motor. On the other hand, when high revolutions per minute are needed and less torque is sufficient, the second gear is driven by the first motor, which provides higher revolutions per minute at the first output drive shaft.

According to a third aspect, the gearbox of the invention provides a further speed at a second output drive shaft, which may be different from the two other speeds, without changing gears and without an additional motor. This second output drive shaft may be used to drive an additional mixing element. The second drive shaft has preferably a fixed speed ratio relative to the first output drive shaft and/or to the second motor, i.e. the speed of the second drive shaft is proportional to the speed of the first output drive shaft and/or to the speed of the second motor. Preferably, the driving of the mixing element is only needed (and used) when the plunger is advanced for dispensing the paste material. It is further preferred that the mixing speed is adjusted in accordance with the output speed of the highly viscous materials which is dependent on the advancing speed of the plunger. The second output drive shaft is thus only rotating when the second motor drives the first output drive shaft. This can be achieved by a direct connection of the second output drive shaft to the output of the second motor. The second output drive shaft provides preferably 200 to 700 revolutions per minute, but can be designed for any speed appropriate to the material(s) being mixed.

The invention preferably provides a gearbox with high torque at low speed, e.g. for pressing out the components, and high speed at relatively low torque which are provided at an output drive shaft, e.g. for rapid positioning the plungers, without using a clutch and without changing gears.

The invention provides the further advantage that both high torque at low speed and high speed with relatively low torque are provided at a first output drive shaft, and a third speed is provided at a second output drive shaft, without using a clutch and without changing gears. This is enabled by the use of a superimposing gear drive providing a permanent connection between the first output drive shaft and two motors as well as a permanent connection between the second motor and the second output drive shaft.

The gearbox of the invention is due to the design including a superimposing gear drive, such as for example a bevel gear drive or a planetary gear drive, which is preferably small and compact and enables a silent and fast change of the direction of rotation at the first output drive shaft. The silent and fast change of the direction of rotation is provided by controlling the two motors, wherein a noisy and slow change of gears is avoided. This fast change of the direction of rotation is advantageous for paste dispensing. The dispensing of highly viscous material with high torque with the first output drive shaft is stopped, by the following step of a fast change in the direction of rotation at the first output drive shaft, which prevents further undesired dispensing of highly viscous material due to the pressure reduction on the paste material.

The invention is unique and different from prior art systems and advantageous in various aspects, wherein two motors serve three purposes. Firstly, high speed is provided by the first motor at the first output drive shaft for positioning the plunger in a short time to the desired position, in both directions, wherein only relatively low torque at the first output drive shaft is sufficient. Secondly, lower speed but with higher torque is provided by the second motor at the first output drive shaft. This is beneficial for driving the plunger or piston and dispensing the material with high viscosity under high pressure. Finally, a third speed is provided, preferably by the second motor at the second output drive shaft, wherein the speed of the second drive shaft has a fixed ratio to the speed of the first output drive shaft, when the first output drive shaft is driven with the second motor only. The third speed is preferable also a low speed for driving the mixing element in the mixer only during dispensation of the paste material. The fixed ratio of the third speed to the low speed is advantageous, since the low speed dispenses the material with a specific speed, and therefore the speed of the mixing tip should be correlated to this dispensing speed.

In a fourth aspect, the invention relates to a method of mixing and extruding viscous materials comprising the steps of:
a) Inserting a cartridge containing one or more viscous materials in a chamber;
b) Activating a first motor to move a plunger from a first position to a second position within the cartridge;
c) Activating a second motor to move the plunger from the second position further within the cartridge to dispense the material.

In step c) the plunger is preferably moved toward a third position so that material is dispensed.

In a fifth aspect, the invention relates to a gearbox, comprising:
  a superimposing gear drive comprising a carrier, a first gear, a second gear and at least one third gear supported by the carrier;
  the second gear being adapted to be driven by a first motor and the first gear or the carrier being adapted to be driven by a second motor.

In a sixth aspect, the invention relates to a drive unit comprising:
  a gearbox according to the invention;
  a first motor and a second motor.

In a seventh aspect, the invention relates to a system for dispensing and/or mixing highly viscous dental products and/or materials comprising a drive unit as and at least one or more of the following features:
  at least one dispensing cartridge preferably containing a dental material or a component thereof;
  at least one plunger adapted to enter an open end of the cartridge and to expel dental material or a component thereof;
  a mixing tip for mixing dental material or merging and mixing components when the dental material or components is/are expelled from the cartridge;
  a first drive train for advancing the plunger by the first output drive shaft;
  a second drive train for advancing the plunger by the second output drive shaft; and
  an electrical or electronic unit for driving and controlling the system.

In an eighth aspect, the invention relates to a system for dispensing and/or mixing highly viscous dental products and/or materials comprising a drive unit as and at least one or more of the following features:
  at least one dispensing cartridge preferably containing a dental material or a component thereof;
  at least one plunger adapted to enter an open end of the cartridge and to expel dental material or a component thereof;
  a mixing tip for mixing dental material or merging and mixing components when the dental material or components is/are expelled from the cartridge;
  a first drive train for advancing the plunger by the first output drive shaft;
  a second drive train for driving the mixing tip by the second output drive shaft; and
  an electrical or electronic unit for driving and controlling the system.

In a ninth aspect, the invention relates to the use of a gearbox, a system and/or a method according to the invention, for dispensing and/or mixing highly viscous dental products and/or materials.

Further preferred features and embodiments of the invention are described in the claims.

It may be provided that the second motor is activated before or when the plunger reaches the second position. Preferably, both motors may work at the same time and can further start and/or stop independently from each other.

It may be provided that the first motor is deactivated when the plunger reaches the second position.

It may be provided that the first position is a position in which the cartridge can be inserted in and/or removed from the chamber.

It may be provided that the second position is a position in which the plunger contacts the material.

It may be provided that the method comprises the step that the load of the first motor is monitored to detect whether the plunger has reached the second position. With this information the steps of activating the second motor and/or deactivating the first motor may be automated.

It may be provided that the method comprises the step that when the dispensing is completed the second motor is deactivated.

It may be provided that the method comprises the step that the second motor is deactivated to stop the dispensing after material has been dispensed, e.g. a given amount which has been initially set by a user.

It may be provided that the method comprises the step that when the dispensing is completed the first motor and/or second motor is activated in opposite directions. This activation results in a back movement of the plungers and may last for a given time, e.g. 1 second so as to remove the pressure on the components in the cartridge, or until the plungers reach the first position, e.g. for cartridge replacement.

It may be provided that the second motor may be used for mixing the material.

It may be provided that the gearbox comprises a first output drive shaft, wherein said first output drive shaft is connected either to the carrier when the first gear is adapted to be driven by the second motor, or to the first gear when the carrier is adapted to be driven by the second motor.

It may be provided that the gearbox comprises a second output drive shaft. Preferably the second output drive shaft is adapted to be connected to a mixing tip.

It may be provided that the gearbox is adapted that the first motor and the second motor, when attached to the gearbox, can drive the first output drive shaft.

It may be provided that the gearbox is adapted to drive the first output drive shaft with a higher torque when be driven with the second motor than when be driven with the first motor.

It may be provided that the gearbox is adapted to drive the first output drive shaft with higher revolutions per minute when be driven with the first motor than when be driven with the second motor.

It may be provided that the gearbox is adapted to drive the first output drive shaft by the first motor and the second motor at the same time.

It may be provided that the gearbox is adapted that the speed of the first output drive shaft is the sum of the product of the speed provided by the first motor and a first transmission ratio and of the product of the speed provided by the second motor and a second transmission ratio. The first and second transmission ratios are defined by the particular construction of the gearbox and its gearwheels, and the first transmission ratio is the ratio between the speeds of the first output drive shaft and the first motor with the second motor standing still, and the second transmission ratio is the ratio between the speeds of the first output drive shaft and the second motor with the first motor standing still.

It may be provided that the gearbox is adapted that when the first output drive shaft is driven by the first motor and the second motor at the same time, the speed of the first output drive shaft is dominated by the first motor and high speed is applied to said first output drive shaft. This may occur for example if the plungers are positioned with low resistance so that the load on the motors is low.

It may be provided that the gearbox is adapted that when the first output drive shaft is driven by the first motor and the second motor at the same time, the speed of the first output drive shaft is dominated by the second motor and high torque is applied to said first output drive shaft. This may occur for example if the plungers are pressed against the components in the cartridge so that the load on the motors is high.

It may be provided that the second output drive shaft has a fixed speed ratio relative to the first output drive shaft and/or relative to the second motor.

It may be provided that the first output drive shaft is adapted for moving a plunger.

It may be provided that the second output drive shaft is adapted for dispensing highly viscous material with higher torque at the first output drive shaft followed by the fast change of the direction of rotation at the first output drive shaft so that further undesired dispensing of highly viscous material is prevented.

It may be provided that the gearbox is adapted that the speed ratio at the first output drive shaft between driving said output drive shaft with the first motor only and driving said output drive shaft with the second motor only, is preferably in the range of 30 to 200, more preferably in the range of 50 to 150, more preferably in the range of 80 to 120, and more preferably 100. It may be provided that the gearbox is adapted that the second output drive shaft rotates only when the second motor is rotating.

It may be provided that the gearbox is adapted that the first output drive shaft is for moving a piston with high speed.

It may be provided that the superimposing gear drive is one of the group of a bevel gear drive, a differential gear drive and a planetary gear drive.

It may be provided that the gearbox is for carrying out the method according to the invention and/or for dispensing and/or mixing highly viscous dental materials.

It may be provided that the drive unit is adapted to provide at the first output drive shaft a torque in the range of 0.5 to 10 Nm, more preferably in the range of 5 to 10 Nm, and more preferably in the range of 8 to 10 Nm.

It may be provided that the drive unit and gearbox is adapted to provide at the second output drive shaft 200 to 700 revolutions per minute. It may be provided that the gearbox, drive unit or system comprises a sensor that produces a signal when the plunger reaches the second position.

It may be provided that the gearbox, drive unit or system comprises:
- a sensor that monitors the speed of the first output drive shaft and/or the speed of the first motor;
- a control unit that is connected to the sensor and produces a signal when the speed reaches a given minimal value and/or decreases faster than a given rate.

It may be provided that the gearbox, drive unit or system comprises:
- a sensor that monitors the current feed to the first motor;
- a control unit that is connected to the sensor and produces a signal when the current reaches a given maximal value and/or increases faster than a given rate.

The control unit may be connected to the first and/or second motor, and the signal produced by the control unit may deactivate the first motor and/or activate the second motor. It may be provided that the gearbox, drive unit or system comprises a switch connected to the control unit, wherein:
- when the switch is in a first mode the first output drive shaft is driven with the high speed to move the plunger from the first position to the second position and from the second position further within the cartridge preferably toward a third position and the material is dispensed; and
- when the switch is in a second mode the dispensing is stopped and/or the first output drive shaft is driven in opposite direction with the high speed to move the plunger back for a given time or distance or toward the second position.

It may be provided that when the switch is in a third mode the first output drive shaft is driven with the high speed to move the plunger toward the second position.

The switch may be a push switch that is in the first mode when pushed, in the second mode when released, and in the third mode when pushed two times in a given period. The switch may also be a slide or a rotary switch that has three switching positions for the three modes.

BRIEF DESCRIPTION OF THE DRAWINGS

Preferred embodiments of the invention are described in more detail below with reference to the attached drawings, which are by way of example only.

DETAILED DESCRIPTION OF PREFERRED EMBODIMENTS

Figure 1:
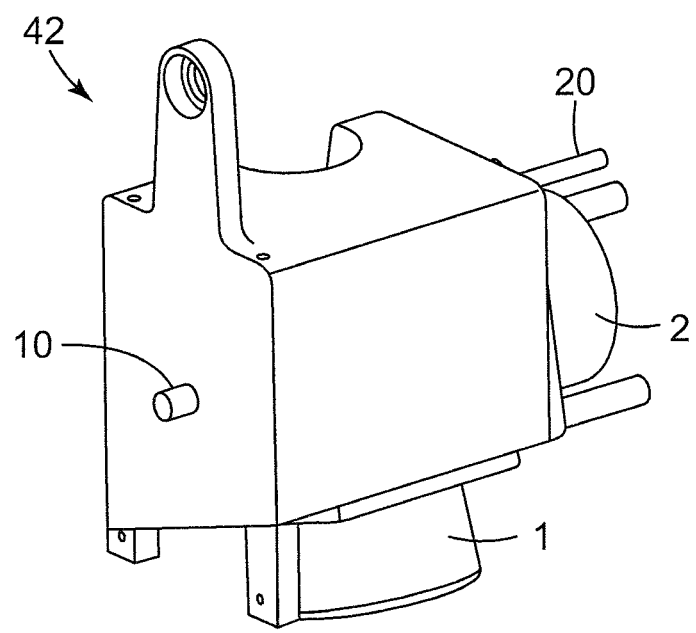
FIG. 1 is a perspective view of a drive unit comprising a gearbox according to a first embodiment.
Figure 2:
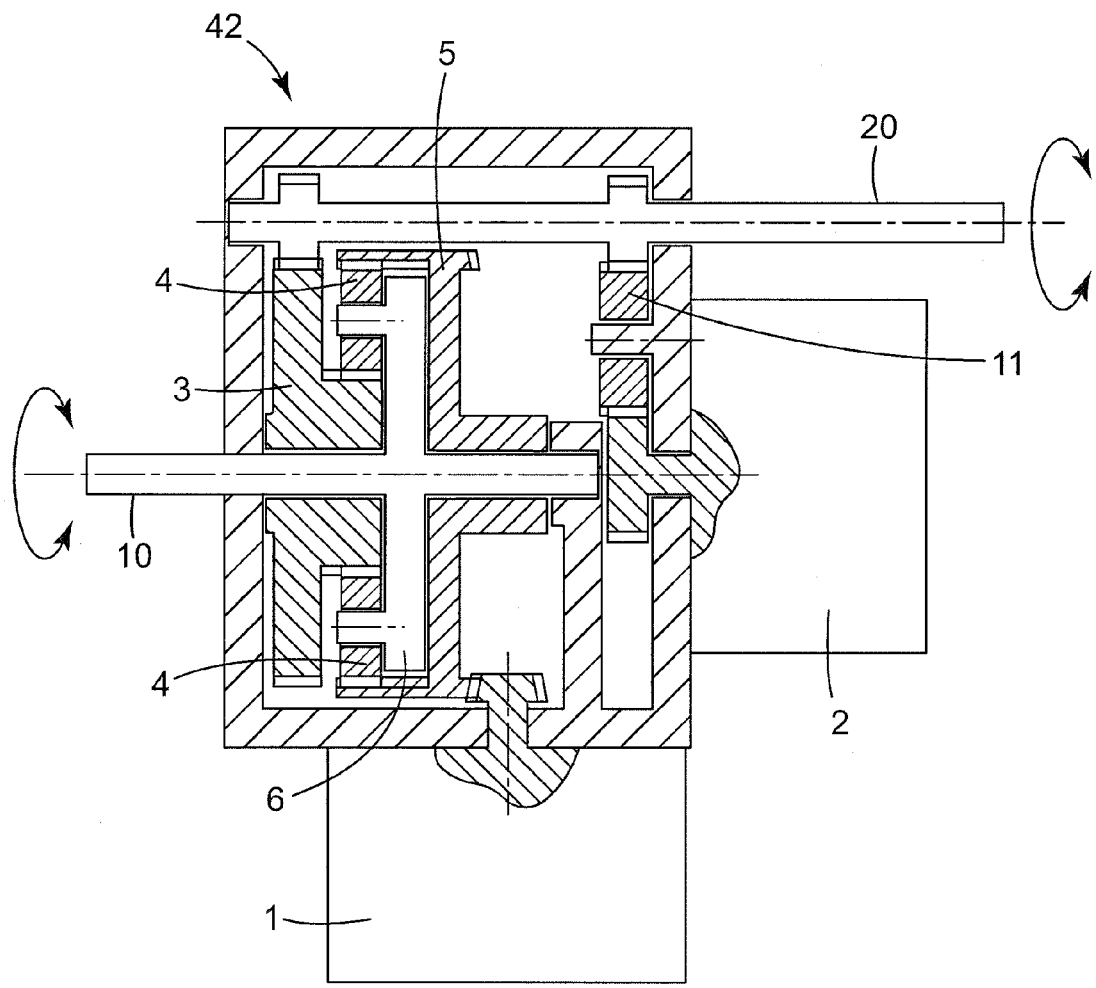
FIG. 2 is a cross-sectional view of the gearbox of the drive unit of FIG. 1.
Figure 3:
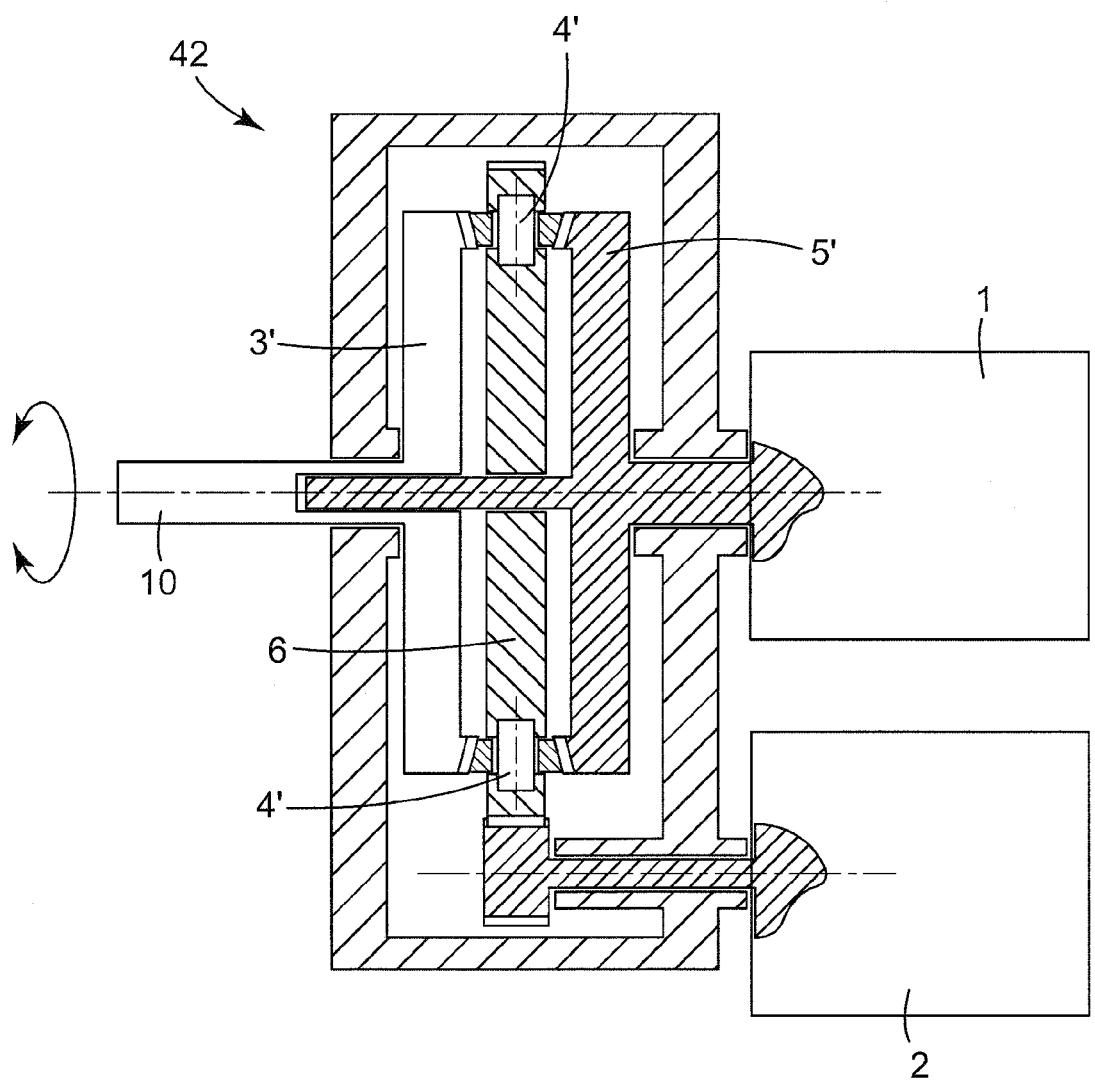
FIG. 3 is a cross-sectional view of a gearbox according to a second embodiment.

Examples of drive units constructed in accordance with the principles of the invention are illustrated in FIGS. 1 to 4. Each of the shown drive units comprises a first motor 1, a second motor 2, a gearbox 42, and a first output drive shaft 10. As can be seen in FIGS. 2 and 3, the gearbox 42 is a superimposing gear drive comprising at least one first gear 3, 3', at least one second gear 5, 5', at least one third gear 4, 4', and a carrier 6 carrying the third gears 4, 4'.

Figure 4:
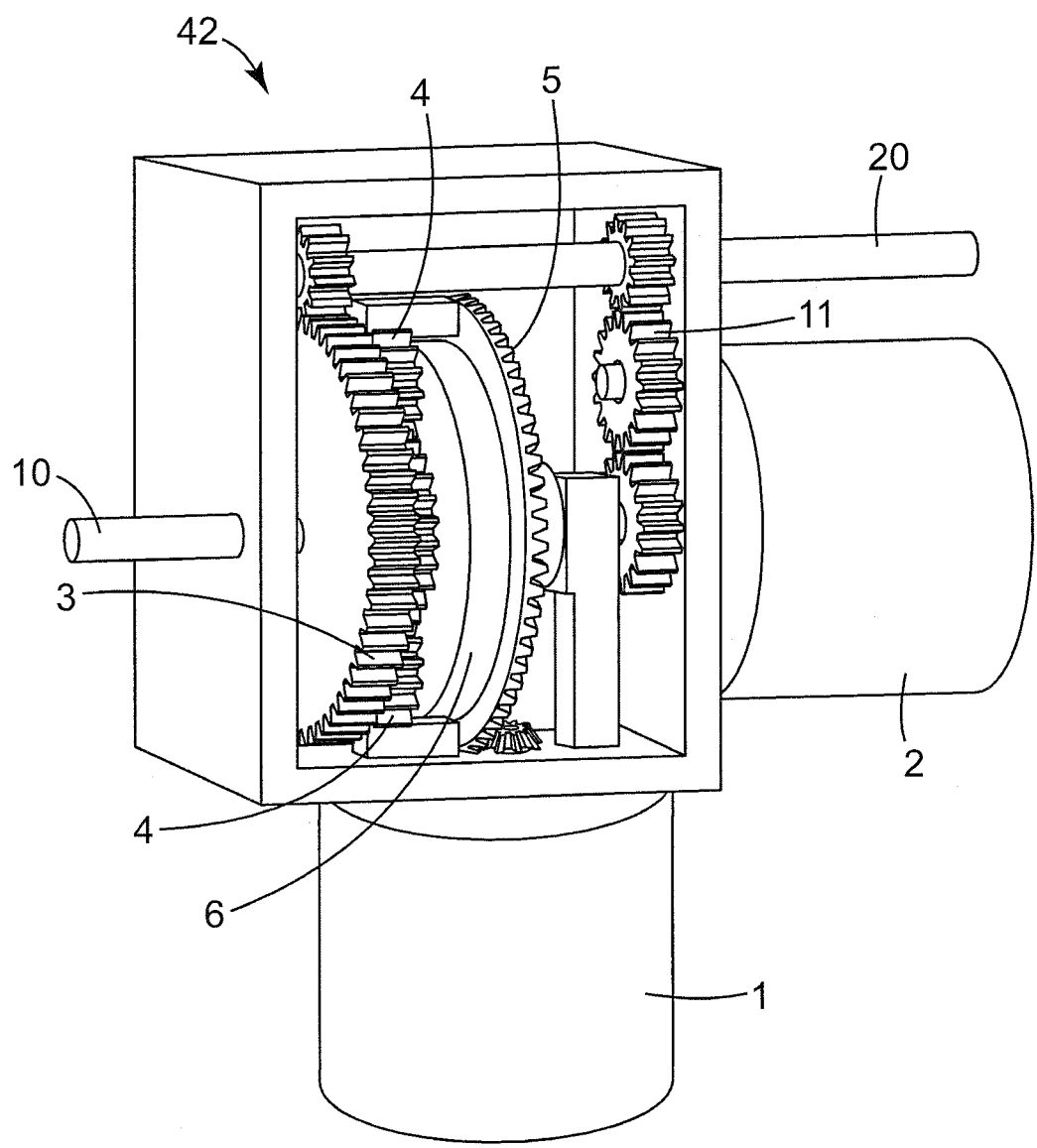
FIG. 4 is a perspective view into the gearbox of the drive unit of FIGS. 1 and 2.

FIGS. 2 and 4 show a first embodiment of a drive unit where the superimposing gear drive is a planetary gear drive. In this case, the above mentioned first, second and third gears correspond to a sun or inner gear 3, a annular or outer gear 5 and a planetary gear 4, respectively.

As shown in FIG. 2, in this first embodiment, the gearbox 42 further comprises a second output drive shaft 20 that is connected to the second motor 2 via a gear 11. The second output drive shaft 20 is further in connection to the inner gear 3. Thus, the inner gear 3 is driven by the second motor 2, providing by a suitable second transmission ratio high torque at the first output drive shaft 10. The first output drive shaft 10 is connectable directly or via a moving means (not shown), to at least one plunger (not shown) for advancing a piston (not shown) in a cartridge 35 (FIG. 5), or for driving the plunger in reverse direction toward a back position. The high torque is necessary at the plunger to supply sufficient force to extrude the highly viscous materials through an outlet opening of the cartridge. For example, the force required to extrude a material with medium viscosity in the field of dental materials, such as 3M™ ESPE™ Position™ Penta™ Quick Vinyl Polysiloxane Preliminary Impression Material (3M ESPE™ order no. 29063) is approximately 1500 Newtons (N) for a standard dispensing speed of 22.5 mm/min. A force may be provided between about 800 N and about 7000 N depending on the preferred dispensing speeds between 22.5 mm/min and 45 mm/min and the material to be extruded. For most of the common dental materials the required force is between 1000 N and 3000 N for dispensing speeds between 22.5 mm/min and 45 mm/min.

The first motor 1 is connected to the annular gear 5 and provides, due to a suitable first transmission ratio, much higher revolutions per minute, as compared with the second motor 2, at the first output drive shaft 10 for moving the plunger fast forward or backward into a desired position. A high speed of the first output drive shaft 10 is advantageous, for instance after the cartridge has been exhausted and the plunger has to be moved toward a first or a back position. After replacing the used cartridge with a new cartridge, the plunger is driven with high speed toward a second or an initial position, in which the plunger is preferably in contact with the highly viscous material.

For the dispensing operation of the refilled highly viscous material, the gearbox 42 is switched from the first motor 1 to the second motor 2 and provides the desired high torque for dispensing the highly viscous pastes or other materials.

Furthermore, it is possible to drive the first output drive shaft 10 with both motors 1, 2 at the same time. The resulting speed at the first output drive shaft 10 is the sum of the two speeds each multiplied by the respective transmission ratio, wherein different driving directions have different algebraic signs as is known in the art. It is therefore possible to drive the plunger with high speed, meaning high revolutions per minute at the first output drive shaft 10, with the two motors at the same time from the back position toward the initial position in which the plunger contacts the highly viscous material. During this fast advancement of the plunger, the sum of the two speeds provided by the first and second motors 1, 2, is dominated by the first motor 1. When the plunger contacts the component, the resistance and therefore the load for both motors 1, 2 increases, but the first motor 1 is less able to handle the increase. This results in an increasing current of the first motor 1 which can be detected by a sensor. The first motor 1 may then be switched off, and the slower advancing speed of the plunger is provided exclusively by the second motor 2. Since the second motor 2 was already running when the first motor 1 is switched off, the high-speed positioning movement of the plunger is not interrupted promptly, but slows down smoothly to the low-speed, high-torque dispensing movement provided by the second motor 2. This results in what might be termed a "phased-out" decrease in speed, or in the reverse situation a "phased-in" increase in speed of the output shaft.

Since the first output drive shaft 10 provides a higher torque when driven with the second motor 2 than when driven with the first motor 1, the plunger is advanced slowly with high torque and dispenses the highly viscous material out of the cartridge. Furthermore, since the second output drive shaft 20 is connected to the second motor 2 with a fixed ratio, the second output drive shaft 20 rotates only when the second motor 2 runs. The output amount of dispensed material is proportional to the advancing speed of the plunger, and therefore to the rotational speed of the first output drive shaft 10. The mixing speed of the mixing tip 30 (FIG. 5), which is connected to the second output drive shaft 20, is therefore automatically adjusted to the dispensing speed due to the fixed ratio between the second output drive shaft 20 and the second motor 2, when the first motor 1 is switched off.

FIG. 3 shows a second embodiment of a drive unit where the superimposing gear drive is a bevel gear drive. In this case, the above-mentioned first, second and third gears are depicted by numerals 3', 5' and 4', respectively.

In this second embodiment, the first motor 1 again drives the second gear 5' whereas the second motor 2 drives the carrier 6. The first gear 3' is connected to the first output drive shaft 10 and has a similar size and design like the second gear 5' due to the bevel gear design.

According to the above and other embodiments of the invention, there is no changing of gears needed to accomplish a large speed ratio or range, i.e. the ratio or range between the high speed and the low speed, at an output drive shaft 10, which is preferable for a dispensing plunger providing either a fast positioning velocity or a high torque for dispensing. This results in less noise, highly reliable mechanics and minimal processing time.

Figure 5:
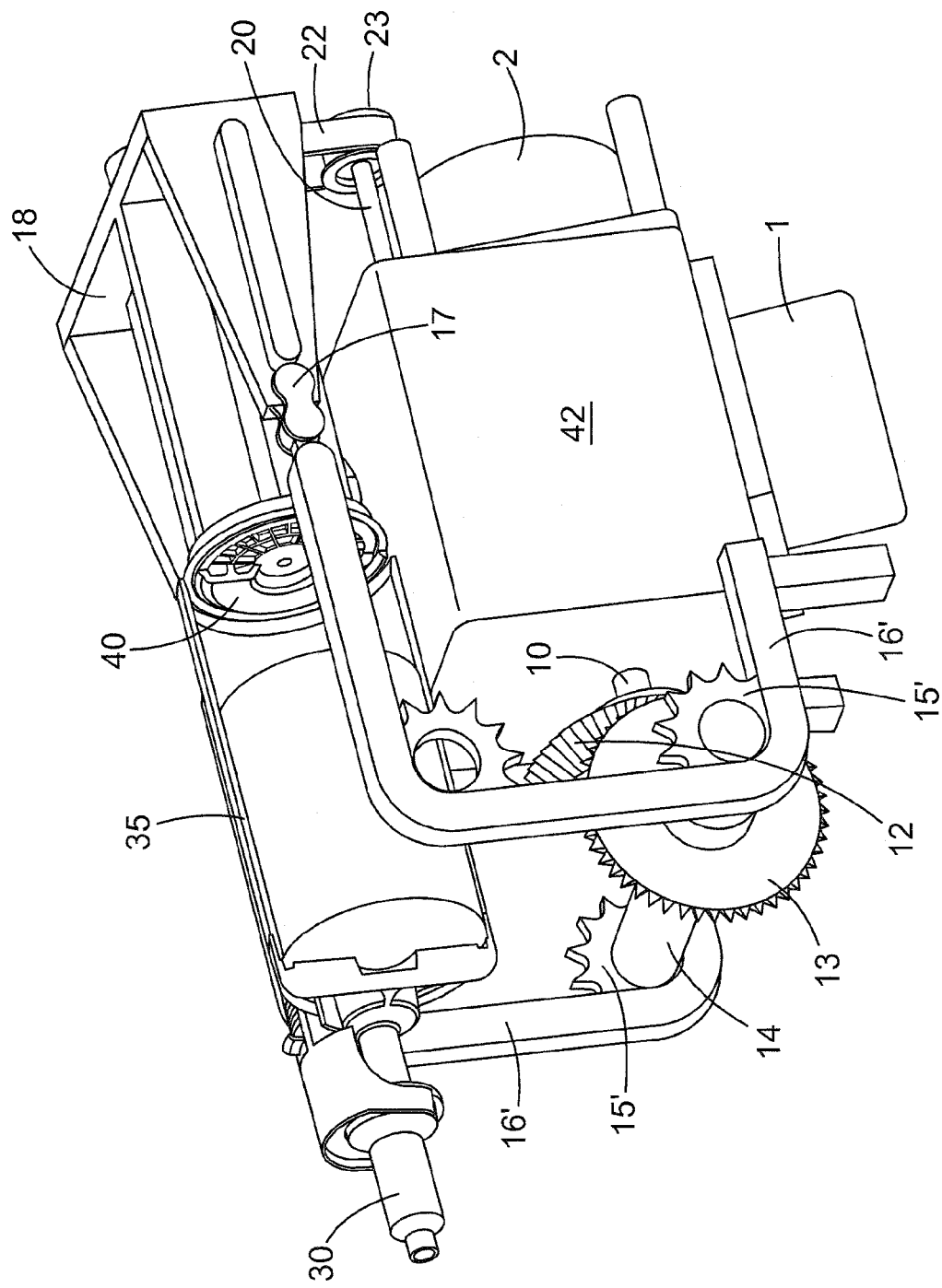
FIG. 5 is a perspective view of a dispensing device with a gearbox according to the present invention.
Figure 6:
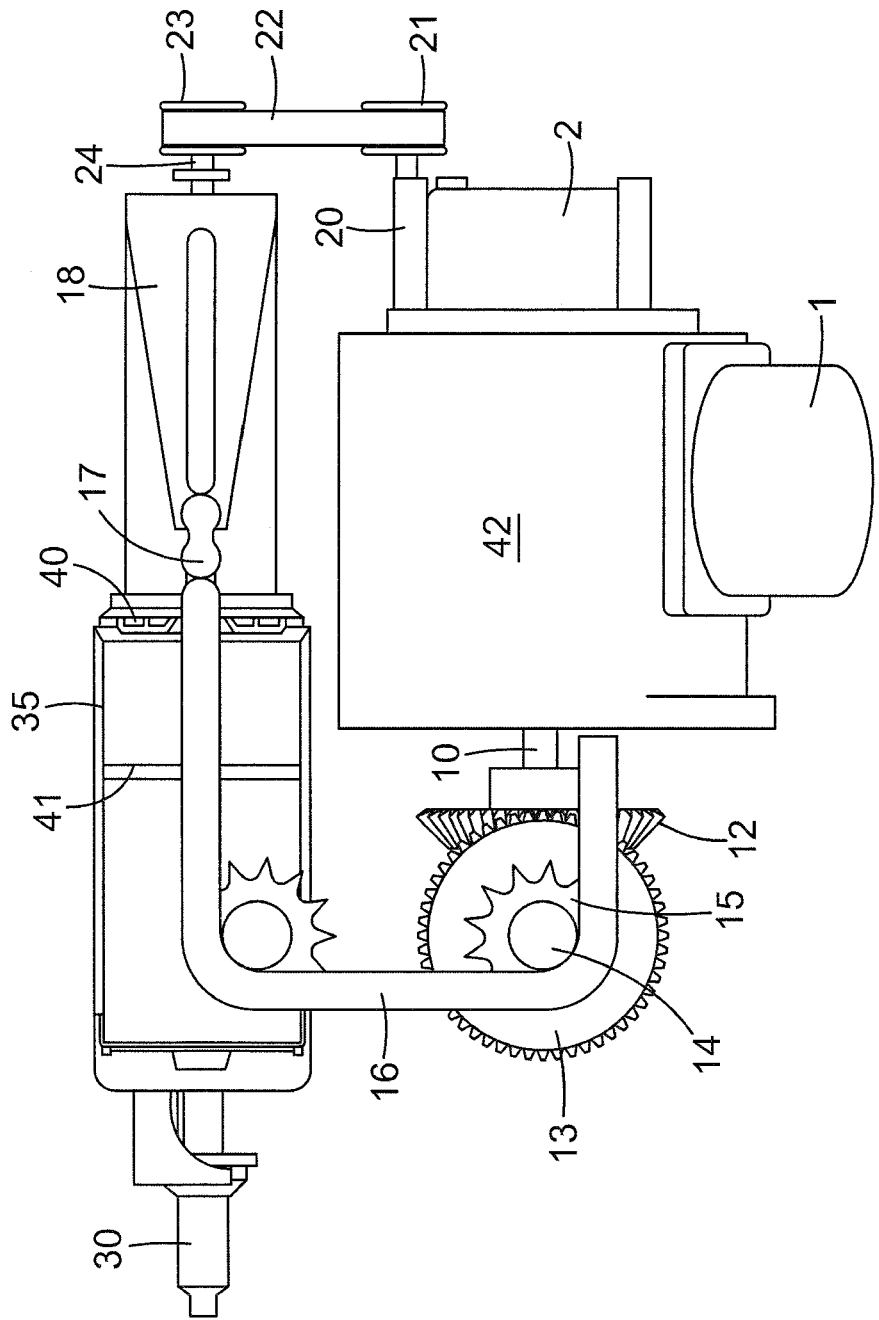
FIG. 6 is a schematic side view of the dispensing device according to FIG. 5.

FIG. 4 shows a perspective view into a gearbox of the drive unit suitable for a dispensing device as illustrated in FIGS. 5 and 6. The dispensing device shown in FIGS. 5 and 6 comprises cartridges which are adapted to receive a quantity of a composition or material to be dispensed. The dispensing device has at least one cartridge 35. In the embodiment according to FIGS. 5 and 6 a first cartridge 35 is visible only. A second cartridge is located behind the first cartridge 35 and can be dimensioned smaller than the first one, depending on the nature of the components. This type of dispensing device comprises two plungers that are advanced by the drive unit. In FIGS. 5 and 6 a first plunger 40 for the first cartridge 35 is visible only. The first plunger 40 is received in an open end of the first cartridge 35 and can bear against a piston 41 within the cartridge (shown in FIG. 6). As the plunger 40 is advanced to move the piston, the piston expels a quantity of material through a front outlet opening of the cartridge.

The plunger 40 can be advanced by the first output drive shaft 10 and by a first drive train. The drive train can comprise gears and sprockets 12-15, a pulling device 16, 17, such as guide rails 16 for guiding chains 17, and a support 18 for the plunger 40. In particular, a first bevel gear 12 can be arranged on the first output drive shaft which meshes with a second bevel gear 13 in order to drive a sprocket shaft 14 with at least one sprocket. Preferably a first sprocket 15 and a second sprocket 15' are provided on both sides as shown in FIG. 5 in order to provide a more uniform movement of support 18 by driving or moving a first chain 17 and a second chain (not shown) being linked on both sides of the support 18. The chains can be guided in a guide rail and further by idle sprockets. Any other driving train being able to transfer the movement from the first output drive shaft 10 for axially moving the plunger 40, such as a gear and a gear rod, can also be used.

The plunger 40 can be further advanced by the second output drive shaft 20 with a second drive train. The second drive train can comprise a driving belt 22 driven by a first pulley 21 which is attached to the second output drive shaft 20. The belt 22 can drive a second pulley 23 rotating a pulley shaft 24 advancing the first plunger 40, e.g. by a screw arrangement between the pulley shaft 24 and a plunger driving shaft within the plunger support 18 which is connected to the plunger 40 (not shown). Preferably the arrangement is such that the plunger 40 does not rotate when being axially advanced by the second output drive shaft 20. This can be realized by a structure preventing rotation of the plunger driving shaft but allowing an axial movement, such as a tongue and groove structure between the plunger driving shaft and the support 18. Any other driving train being able to transfer the movement from the second output drive shaft 20 for axially moving the plunger 40, such as a plurality of gears or a gear and a gear rod, can also be used.

The embodiment of the dispensing device shown in FIG. 5 comprises two cartridges for mixing and dispensing dental compositions of two components. These two components are expelled from their respective cartridges 35 out into a mixing tip 30 where the required dental material is mixed. The mixing tip 30 can be dynamic and may be coupled to the second drive shaft 20 of the gear box for rotating an inner body of the mixing tip 30.

The second drive train 21-24 can drive the dynamic mixing tip 30 with a rotating screw inside the tip transporting and further mixing two or in other embodiments more components being expelled from the different cartridges. The driving can be realized by a tip rotating shaft (not shown) being driven by the pulley shaft 24 and a gear arrangement between the pulley shaft and the tip rotating shaft. The gear ratio of this gear arrangement can be adapted to correspond to the different amounts of components being expelled by the cartridges and then merged in the mixing tip 30.

Preferably the first drive train 12-17 and the second drive train 21-24 are arranged to operate independently from each other as in the embodiment shown in FIGS. 5 and 6. However, a driving train can also be provided superimposing the movements of the first output drive shaft 10 and the second output drive shaft 20.

The gearbox used in a suitable device allows a dentist to fill a tray with for example dental impression material in a significantly reduced amount of time, enhancing the benefit to the dentist combined with automated and fast cartridge exchange.

The invention has now been described with reference to several embodiments thereof. It will be apparent to those skilled in the art that many changes can be made in the embodiments described without departing from the scope of the invention. Thus the scope of the invention should not be limited to the structures described in this application, but only by structures described by the language of the claims and the equivalents of those structures.

The invention claimed is:

1. A method of mixing and dispensing viscous materials, comprising the steps of:
    a) Inserting a cartridge containing one or more viscous materials in a chamber;
    b) Activating a first motor to move a plunger via an output drive shaft from a first position to a second position within the cartridge;
    c) Activating a second motor to move the plunger via said output drive shaft from the second position further within the cartridge to dispense the material,
    wherein the speed of said output drive shaft is (i) the sum or (ii) the difference of the driving speed of the first motor and the second motor.

2. Method according to claim 1, wherein the second motor is activated before or when the plunger reaches the second position.

3. Method according to claim 1, wherein both motors are working at the same time.

4. Method according to claim 1, wherein the first motor is deactivated before or when the plunger reaches the second position.

5. Method according to claim 1, wherein the first position is a position in which the cartridge can be inserted in and/or removed from the chamber, and the second position is a position in which the plunger contacts the material.

6. Method according to claim 1, wherein the second position is a position in which the plunger contacts the material.

7. Method according to claim 1, further comprising providing a sensor to monitor the load of the first motor to detect whether the plunger has reached the second position.

8. Method according to claim 1, comprising the step of deactivating the second motor after materials has been dispensed.

9. Method according to claim 1, comprising the step of deactivating the second motor to stop the dispensing.

10. Method according to claim 1, comprising the step activating the first motor and/or second motor in opposite directions when the dispensing is completed.

11. Method according to claim 1, wherein the second motor is used for mixing the material.

12. Method according to claim 1, comprising the steps of:
    a1) driving one of the first motor or the second motor; and
    b1) activating the other one of the first motor or second motor to accelerate the drive shaft to a higher speed; and/or:
    a2) driving the first motor and the second motor at the same time; and
    b2) deactivating one of the first motor or second motor to decelerate the drive shaft to a lower speed.

* * * * *

UNITED STATES PATENT AND TRADEMARK OFFICE
CERTIFICATE OF CORRECTION

PATENT NO. : 8,424,718 B2
APPLICATION NO. : 12/977714
DATED : April 23, 2013
INVENTOR(S) : Ingo Wagner et al.

Page 1 of 1

It is certified that error appears in the above-identified patent and that said Letters Patent is hereby corrected as shown below:

In the Specifications:

Column 1
Line 10                Delete "U.S." and insert -- U.S.C. --, therefor.

Column 8
Lines 41-43            Delete "It may be provided that.....to the control unit, wherein:" and insert the same: -- It may be provided that.....to the control unit, wherein: -- on Col. 8, Line 42 as a new Paragraph.

Signed and Sealed this
Sixth Day of August, 2013

Teresa Stanek Rea
*Acting Director of the United States Patent and Trademark Office*